United States Patent
D'Augustine et al.

(10) Patent No.: US 11,798,687 B2
(45) Date of Patent: Oct. 24, 2023

(54) INTEGRATED DIAGNOSTIC TEST REQUISITION AND CLINICAL DECISION SUPPORT

(71) Applicant: STANDARD MOLECULAR, INC., Cambridge, MA (US)

(72) Inventors: James Mark D'Augustine, Acton, MA (US); Jeffrey Scott Sopko, New Milford, CT (US)

(73) Assignee: Standard Molecular, Inc., Cambridge, MA (US)

( * ) Notice: Subject to any disclaimer, the term of this patent is extended or adjusted under 35 U.S.C. 154(b) by 0 days.

(21) Appl. No.: 17/347,296

(22) Filed: Jun. 14, 2021

(65) Prior Publication Data
US 2022/0044810 A1 Feb. 10, 2022

Related U.S. Application Data

(60) Provisional application No. 63/061,531, filed on Aug. 5, 2020.

(51) Int. Cl.
*G16H 50/20* (2018.01)
*G16H 10/60* (2018.01)
*G16H 15/00* (2018.01)

(52) U.S. Cl.
CPC ............. *G16H 50/20* (2018.01); *G16H 10/60* (2018.01); *G16H 15/00* (2018.01)

(58) Field of Classification Search
CPC ........ G16H 50/20; G16H 15/00; G16H 10/60; G16H 10/40; G16H 40/63; G16H 40/20
See application file for complete search history.

(56) References Cited

U.S. PATENT DOCUMENTS

| | | | | |
|---|---|---|---|---|
| 2001/0051879 | A1* | 12/2001 | Johnson | G16H 10/40 707/999.001 |
| 2004/0153822 | A1 | 8/2004 | Arcand et al. | |
| 2008/0082357 | A1* | 4/2008 | Schmitt | G16H 40/63 705/2 |
| 2008/0270438 | A1* | 10/2008 | Aronson | G16H 10/60 |
| 2009/0080408 | A1* | 3/2009 | Natoli | G16Z 99/00 370/351 |

(Continued)

OTHER PUBLICATIONS

Yutaka Saeki, et al., "Reuse of Bibliography in a Database using Customized Output Rule" 0-7803-7724-9103/S17.00 @ 2003 IEEE (Year: 2003).*

(Continued)

*Primary Examiner* — Gregory D. Moseley

(57) ABSTRACT

Methods and systems for providing integrated diagnostic test requisition and clinical decision support are disclosed. A request for diagnostic test information for a patient is received from an electronic medical records (EMR) system. Diagnostic tests appropriate for the patient are determined based on the request, and fields of a user interface for requesting the tests are populated based on test definitions corresponding to each test. Test requisitions are generated and transmitted to a test provider in a test-provider format, and results are received from the test provider and standardized. Courses of action appropriate for the patient are determined and proposed based on the standardized results and biomarker definitions related to the patient's condition.

22 Claims, 7 Drawing Sheets

(56) References Cited

U.S. PATENT DOCUMENTS

| | | | |
|---|---|---|---|
| 2013/0197943 A1* | 8/2013 | Conlin | G06F 16/2471 |
| | | | 705/2 |
| 2013/0226621 A1 | 8/2013 | Van Der Zaag et al. | |
| 2014/0316813 A1 | 10/2014 | Bauer | |
| 2016/0314249 A1* | 10/2016 | Dunleavy | G16H 10/60 |
| 2019/0304582 A1* | 10/2019 | Blumenthal | G16H 40/67 |
| 2020/0043584 A1 | 2/2020 | Coe et al. | |
| 2020/0118164 A1* | 4/2020 | DeFrank | G06Q 30/0269 |
| 2020/0126663 A1 | 4/2020 | Lucas et al. | |

OTHER PUBLICATIONS

International Search Report for International Application No. PCT/US2021/037292 dated Sep. 24, 2021, 2 pages.

* cited by examiner

FIG. 2
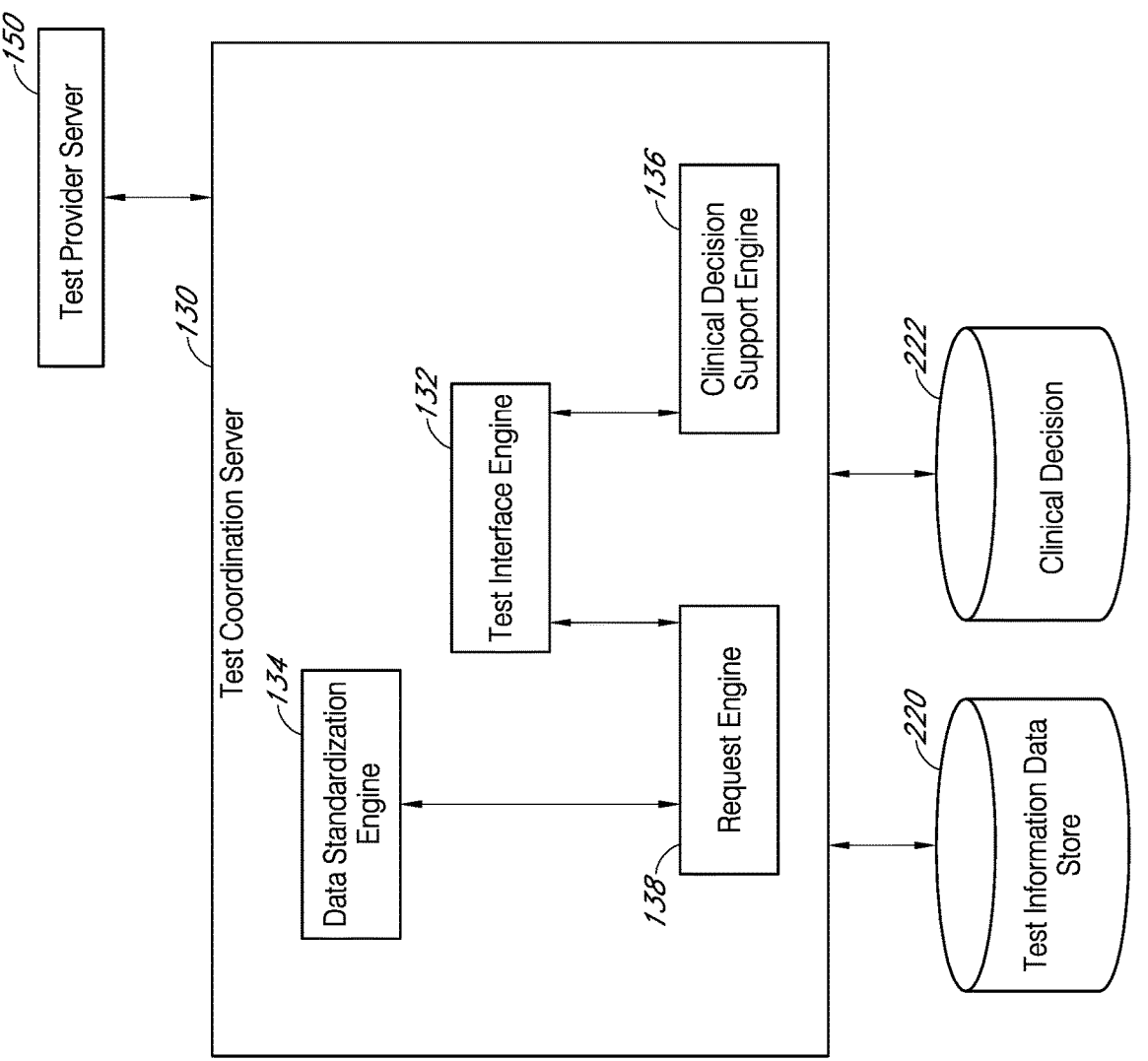
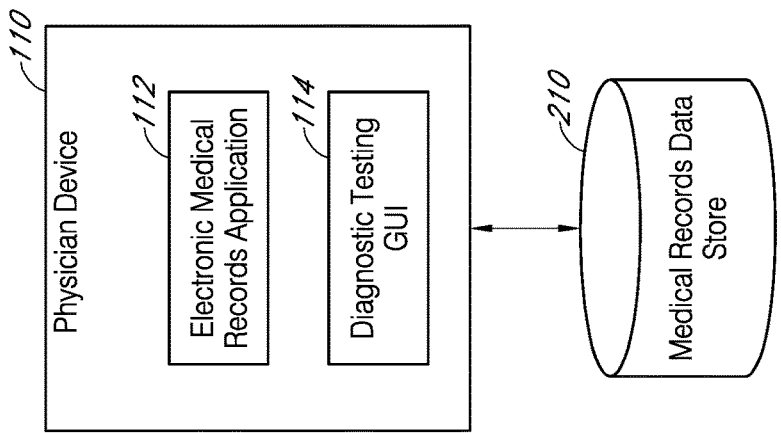

FIG. 3

Hub Order Entry                          ⊖assistant1

*— 300*

310
ORDER   STATUS   LAST STATUS CHANGE   CREATED   TEST NAME   VERSION   LAB NAME   ADDRESS
100000150   UNSUBMITTED   2020-02-26 12:04 PM   2020-02-26 12:04 PM   OncoMP-10001   v1.0   OncoMP Lab   1 Main Street
                                                                                                                       Some City, MA 12345
PHONE   [Reference]
(555) 555-5555

Case Patient

320
PATIENT   SEX   DATE OF BIRTH   MRN   SOURCE
Ethyl Marie Mertz (1234567)   Female   1925-12-31T00:00:00   1234567   medical record [Detail]

360
▷ A. Reasons for Running this Test

▷ B. Clinical Information

▷ C. Specimen Information

▷ D. Billing Information

Practice

330
PRACTICE NAME   ADDRESS   PHONE
Acme Oncology

Ordering Physician

340
PRACTITIONER   NPI   SPECIALTY
Olivia Ann Oskerwitz, MD, PhD   1234567891   [Add] [Detail] [Remove]

Notes

Enter any notes you wish to record. None of these notes will be delivered to the lab.
NOTE   LAST UPDATED   ENTERED BY   [Add]

350
[Cancel Order]                                                                 [Sign] [Save] [Close]

FIG. 4

▼ B. Clinical Information

B.1. Disease

Select or enter the patient's disease relevant for this test.

Disease

| NAME | ORDERPATIENT | CONDITIONCODE | CONDITIONOTHER | OBJECTSOURCECODE | |
|---|---|---|---|---|---|
| 4234568 | Ethyl Marie Mertz (1234567) | Cancer en cuirasse (disorder) | | medical record | [Detail] [Remove]  +MR +UA +AE |

B.2. Metastasis (Lymph Nodes)

B.2.1. Status

Select one status classification or check "Status Unknown". If you check "Status Unknown" or choose "Lymph Nodes Contain Isolated Tumor Cells Only [N0(i+)]", the patient will be analyzed and reported as Lymph Node-Negative. —440

Lymph Node Tumor Summary - Status Classification

| NAME | ORDERPATIENT | OBSERVATIONCODE | | OBJECTSOURCECODE | |
|---|---|---|---|---|---|
| 6234567 | Ethyl Marie Mertz (1234567) | Lymph Node-Positive (N1 or N1mi; 1-3 positive nodes) | | medical record | [Detail] [Remove]  +MR +UA +AE |

Lymph Node Tumor Status - Unknown

☐ Status Unknown

Lymph Node Tumor Details

Largest Tumor Size (cm)

⎱ 435

Highest Tumor Grade (Nottingham or Elston)

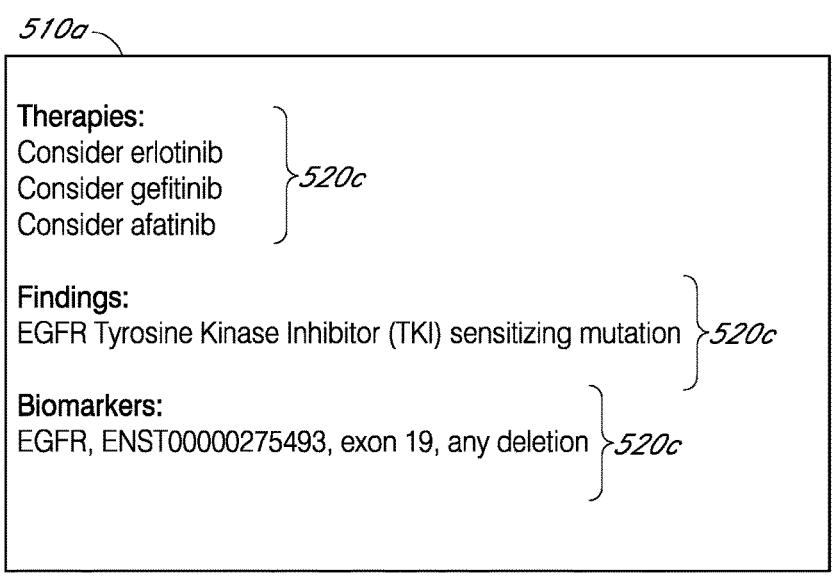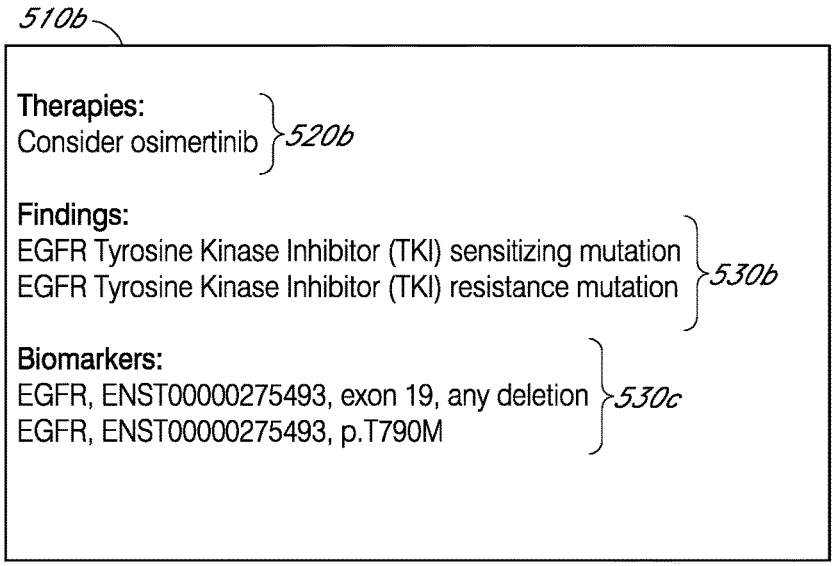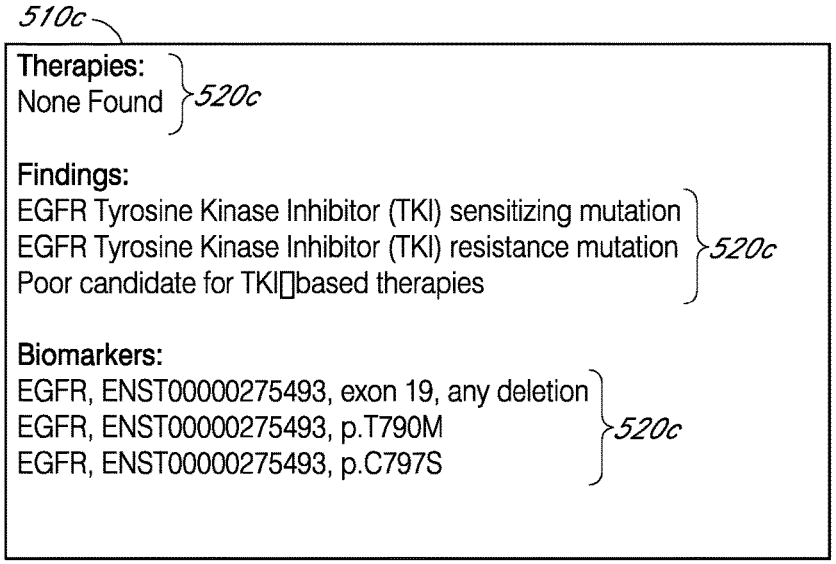
FIG. 5

INTEGRATED DIAGNOSTIC TEST REQUISITION AND CLINICAL DECISION SUPPORT

CROSS-REFERENCE TO RELATED APPLICATIONS

The present application claims priority to and the benefit of the U.S. Provisional Patent Application No. 63/061,531, filed Aug. 5, 2020, titled "Integrated Diagnostic Test Requisition and Clinical Decision Support," which is hereby incorporated by reference in its entirety as if fully set forth below and for all applicable purposes.

FIELD

This description is generally directed towards systems and methods for ordering, analyzing, and acting upon medical diagnostic tests. More specifically, systems and methods for aiding in the selection of relevant diagnostic tests based on patient data, requesting the diagnostic tests from test providers, and analyzing test results to suggest appropriate diagnoses, prognoses, and treatment options are disclosed herein.

BACKGROUND

A physician treating a patient for a medical condition is often required to interact with a number of disconnected or loosely connected systems to order diagnostic tests for the patient and receive test results. The physician may interact with an electronic medical records (EMR) system to access and store information related to the patient's medical history. The physician may order diagnostic tests for the patient from any number of labs, each with different forms and requirements. The selection of which lab to choose for a particular diagnostic test may be driven not only by the type of diagnostic test required, but by financial considerations, including those related to the patient's medical insurance. The physician may print a paper form with the diagnostic test orders for the patient to carry to the lab, fax the orders to lab, or submit the order electronically through a portal provided by the lab. Similarly, the physician may receive the test results via fax or a lab-specific portal. Upon receiving the test results, the physician may again access the EMR system to record the results.

In addition to choosing appropriate diagnostic tests for the patient's condition, ordering the tests, and receiving and recording the results of the tests, the physician interprets the results and select an appropriate course of treatment for the patient based on the results. The selection of an appropriate test may be complex, particularly in the field of oncology where a type of cancer may be associated with many different biomarkers, each associated with different treatment options of varying efficacy, which may result in patients not being tested for biomarkers that may be helpful in determining an appropriate course of treatment. Test results for the same biomarker from different labs may be reported in a different format, complicating both the interpretation of the tests by the physician, and any attempts at automation directed toward recording and/or processing the results. Once the physician has read and interpreted the results, the selection of an appropriate course of treatment involves not only a consideration of the test results, but also of the patient's medical history, comorbidities, and recently developed medical knowledge. Accordingly, integrated methods of guiding the selection of appropriate tests for a patient, selecting a lab to perform the testing, completing the entry of data required by the lab, transmitting the test orders to the lab, receiving the results, presenting the results in a standardized format, and suggesting effective treatment options for the patient are needed.

SUMMARY

In one aspect, a system for providing clinical decision support (CDS) is disclosed. The system includes a test information data store, a CDS data store, and a computing device.

The test information data store stores diagnostic test definition data including a plurality of test definitions.

The CDS data store stores data associated with a plurality of biomarker definitions and related medical conditions.

The computing device is communicatively coupled to the test information data store and the CDS data store and hosts a request engine, a CDS engine, a data standardization engine, and a test interface engine.

The request engine is configured to receive a request for diagnostic test information associated with a patient from an electronic medical records (EMR) system. The request includes patient data. The request engine is further configured to transmit one or more test requisitions and receive one or more results corresponding to each of the one or more test requisitions.

The CDS engine is configured to determine one or more diagnostic tests based on the request. Each diagnostic test is associated with a test definition of the plurality of test definitions. The CDS engine is further configured to determine, based on one or more standardized results and the data associated with the plurality of biomarker definitions and related medical conditions, one or more courses of action.

The data standardization engine is configured to convert data associated with each of the one or more diagnostic tests into a test data requisition format associated with a test provider. The data standardization engine is further configured to generate the one or more standardized results based on the received one or more results. Generating the standardized results includes converting data associated with each result of received one or more results into a uniform data format.

The test interface engine is configured to populate one or more fields of a plurality of graphical user interface (GUI) fields. The test interface engine is further configured to generate the one or more test requisitions based on the request.

In another aspect, a method for providing CDS is disclosed. One or more processors receive, from an EMR system, a request for diagnostic test information associated with a patient. The request includes patient data.

The one or more processors determine one or more diagnostic tests based on the request. Each diagnostic test is associated with a test definition of a plurality of test definitions.

The one or more processors populate one or more fields of a plurality of GUI fields based on the request and patient data.

The one or more processors convert data associated with each of the one or more diagnostic tests into a test data requisition format associated with a test provider.

The one or more processors generate one or more test requisitions based on the request, transmit the one or more test requisitions, and receive one or more results corresponding to each of the one or more test requisitions.

The one or more processors generate one or more standardized results based on the received one or more results. The generating of the standardized results includes converting data associated with each result of the received one or more results into a uniform data format.

The one or more processors determine one or more courses of action based on the one or more standardized results and data associated with a plurality of biomarker definitions and related medical conditions.

In yet another aspect, a non-transitory machine-readable medium stores machine-readable instructions executable to cause a machine to perform operations for providing clinical decision support. The operations include receiving, by one or more processors from an EMR system, a request for diagnostic test information associated with a patient. The request includes patient data.

The operations further include determining, by the one or more processors, one or more diagnostic tests based on the request. Each diagnostic test is associated with a test definition of a plurality of test definitions.

The operations further include populating, by the one or more processors, one or more fields of a plurality of GUI fields based on the request and the patient data.

The operations further include converting, by the one or more processors, data associated with each of the one or more diagnostic tests into a test data requisition format associated with a test provider.

The operations further include generating, by the one or more processors, one or more test requisitions based on the request, transmitting the one or more test requisitions, and receiving one or more results corresponding to each of the one or more test requisitions.

The operations further include generating, by the one or more processors, one or more standardized results based on the received one or more results. The generating of the standardized results includes converting data associated with each result of the received one or more results into a uniform data format.

The operations further include determining, by the one or more processors, one or more courses of action based on the one or more standardized results and data associated with a plurality of biomarker definitions and related medical conditions.

BRIEF DESCRIPTION OF THE DRAWINGS

For a more complete understanding of the principles disclosed herein, and the advantages thereof, reference is now made to the following descriptions taken in conjunction with the accompanying drawings, in which:

FIG. 2 is a block diagram illustrating a test coordination server, in accordance with various embodiments.

FIG. 3 is an illustration of an exemplary order entry user interface for ordering a diagnostic test, in accordance with various embodiments.

FIG. 4 is an illustration of an exemplary order entry user interface for entering clinical data for a diagnostic test order, in accordance with various embodiments.

FIG. 5 is an illustration of exemplary results analysis user interfaces for providing analysis of diagnostic test results and recommending courses of treatment, in accordance with various embodiments.

Figure 1:
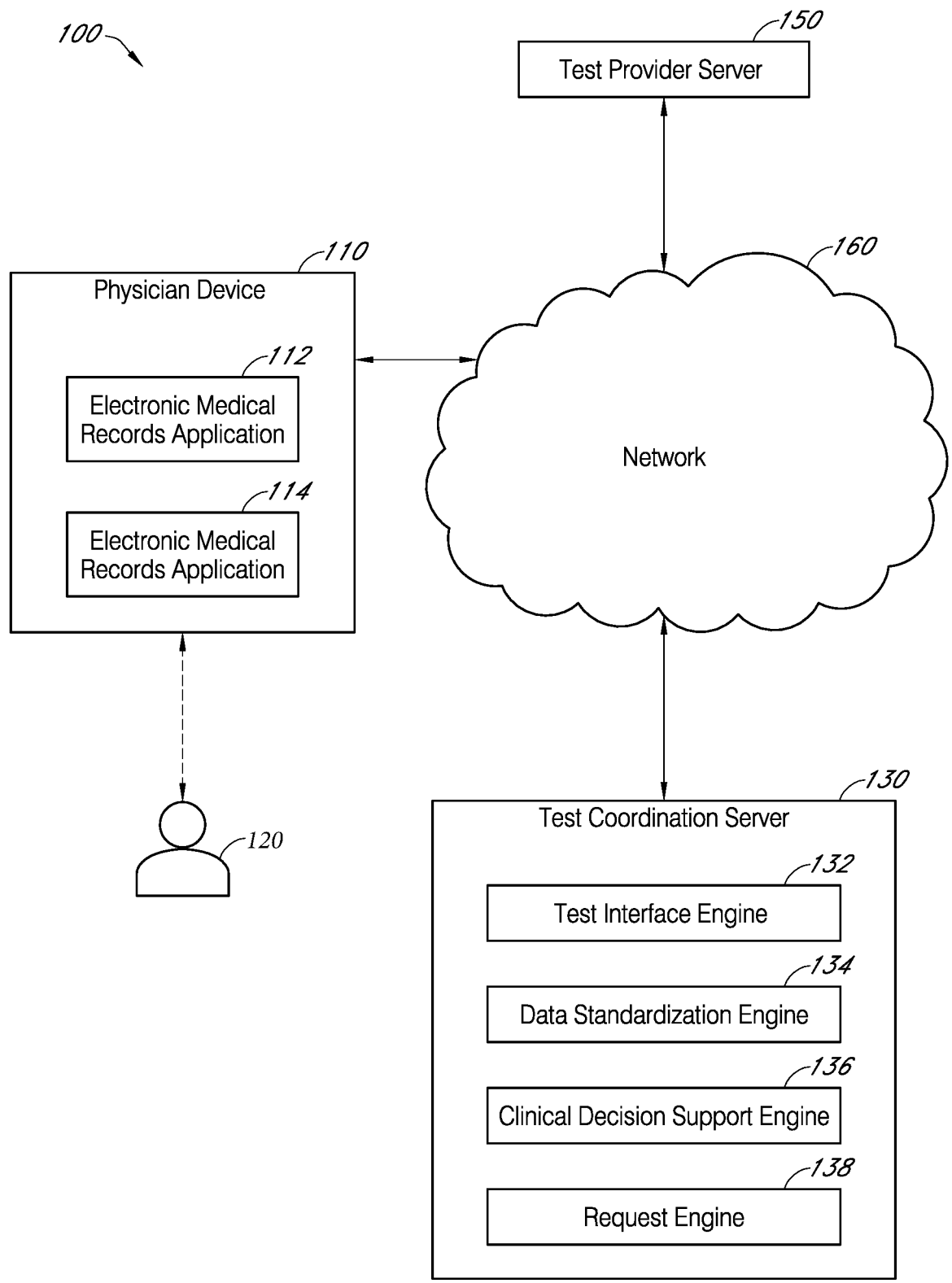
FIG. 1 is a bock diagram illustrating a test requisition and CDS system, in accordance with various embodiments.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DETAILED DESCRIPTION

This specification describes various exemplary embodiments of systems and methods for providing CDS with respect to choosing and ordering diagnostic tests, receiving and interpreting diagnostic test results, and determining appropriate courses of treatment for a patient's condition. As described in detail with respect to FIGS. 1 and 2 below, embodiments of the present disclosure provide medical professionals with a way of determining which diagnostic tests are most appropriate for a patient, ordering those tests from one or more test providers in a provider-agnostic way that provides physicians with a standardized interface for requesting tests from any supported provider, and receiving the results from the test providers. Embodiments of the present disclosure also analyze the results, providing physicians with recommended courses of action that are selected while accounting for individual characteristics of the patient beyond merely a diagnosis (e.g., comorbidities, age, allergies, and family medical history). Embodiments of the present disclosure provide guidance to the physician at different steps of the diagnostic test requisition and analysis process, automating much of the data entry involved in ordering a diagnostic test.

Existing systems and methods of ordering diagnostic tests and receiving results may involve disjoint processes and technologies. As discussed above, a physician may use an EMR system to store and retrieve patient data, a fax machine or a test-provider-specific portal to order diagnostic tests and receive results, which may then be entered into the EMR system. In contrast to those systems and methods, embodiments of the present disclosure may integrate with existing EMR systems and provide a single, test-provider-agnostic way of ordering diagnostic tests and receiving results, while guiding the selection and interpretation of diagnostic tests, reducing the time and complexity involved in ordering diagnostic tests and receiving test results. Furthermore, by providing CDS to physicians at different stages of the diagnostic testing process, from test selection to results interpretation, embodiments of the present disclosure may improve patient outcomes by assisting doctors in the selection of the most appropriate tests for a patient and the most appropriate treatment options for the patient.

The disclosure, however, is not limited to these exemplary embodiments and applications or to the manner in which the exemplary embodiments and applications operate or are described herein. Moreover, the figures may show simplified or partial views, and the dimensions of elements in the figures may be exaggerated or otherwise not in proportion. In addition, as the terms "on," "attached to," "connected to," "coupled to," or similar words are used herein, one element (e.g., a layer, etc.) can be "on," "attached to," "connected to," or "coupled to" another element regardless of whether the one element is directly on, attached to, connected to, or coupled to the other element or there are one or more intervening elements between the one element and the other element. In addition, where reference is made to a list of elements (e.g., elements a, b, c), such reference is intended to include any one of the listed elements by itself, any combination of less than all of the listed elements, and/or a combination of all of the listed elements. Section divisions in the specification are for ease of review only and do not limit any combination of elements discussed.

Unless otherwise defined, scientific and technical terms used in connection with the present teachings described herein shall have the meanings that are commonly understood by those of ordinary skill in the art. Further, unless otherwise required by context, singular terms shall include pluralities and plural terms shall include the singular. Generally, nomenclatures utilized in connection with, and techniques of, chemistry, biochemistry, molecular biology, pharmacology and toxicology are described herein are those well-known and commonly used in the art.

As used herein, "substantially" means sufficient to work for the intended purpose. The term "substantially" thus allows for minor, insignificant variations from an absolute or perfect state, dimension, measurement, result, or the like such as would be expected by a person of ordinary skill in the field but that do not appreciably affect overall performance. When used with respect to numerical values or parameters or characteristics that can be expressed as numerical values, "substantially" means within ten percent.

The term "ones" means more than one.

As used herein, the term "plurality" can be 2, 3, 4, 5, 6, 7, 8, 9, 10, or more.

A reference to an element in the singular is not intended to mean "one and only one" unless specifically stated, but rather "one or more." As used herein, the term "about" used with respect to numerical values or parameters or characteristics that can be expressed as numerical values means within ten percent of the numerical values. For example, "about 50" means a value in the range from 45 to 55, inclusive.

FIG. 1 is a block diagram illustrating a test requisition and CDS system 100, in accordance with various embodiments.

The system includes a physician device 110, a test coordination server 130, and a test provider server 150, all of which may communicate via a network 160. The network 160, in various embodiments, may be implemented as a single network or a combination of multiple networks. For example, in various embodiments, the network 160 may include the Internet and/or one or more intranets, landline networks, wireless networks, and/or other appropriate types of communication networks. In another example, the network 160 may comprise a wireless telecommunications network (e.g., cellular phone network) adapted to communicate with other communication networks, such as the Internet.

The physician device 110, in various embodiments, may be used by a user 120 (e.g., a physician or other medical professional) to interact with the test coordination server 130. For example, the user may use the physician device 110 to enter and review patient information, order diagnostic tests, review diagnostic test results, and review treatment options and other medical information.

The physician device 110, in various embodiments, may be implemented using any appropriate combination of hardware and/or software configured for wired and/or wireless communication over the network 160. In various implementations, the user device 110 may include at least one of a personal computer (PC), wireless cellular phone, tablet device, etc.

The physician device 110, in various embodiments, may include an EMR application 112 (also referred to as an EMR system). The EMR system may provide an interface for entering, storing, and reviewing patient information. The patient information may include, for example, biographical information about a patient (e.g., name, birth date, etc.), medical history (e.g., medical conditions, allergies, surgeries, hospitalizations, etc.) including family medical history, medications taken by the patient, insurance information, and any number of other types of information related to a patient. The EMR application 112 may be configured to provide access to various capabilities of the test coordination server 130 to allow a user 120 to choose and order diagnostic tests, receive and view test results, and view recommended courses of actions. For example, activating a user interface (UI) element in a GUI of the EMR application 112 (e.g., pressing a button or following a hyperlink) may launch a diagnostic testing GUI 114 providing access to the capabilities of the test coordination server 130. The diagnostic testing GUI 114 may be presented as part of the EMR application 112. For example, the diagnostic testing GUI 114 may be integrated as an extension, plugin, or component of the EMR application 112 so that the diagnostic testing GUI 114 is presented as part of the EMR application 112 GUI, and interacting with the diagnostic testing GUI 114 results in various requests being sent to and various responses being received from the test coordination server 130. In some embodiments, the diagnostic testing UI may be hosted by the test coordination server. For example, the EMR application 112 may present, in an embedded web browser, the diagnostic testing GUI 114 hosted by the test coordination server. In some embodiments, launching the diagnostic testing GUI 114 may open a web browser in a new window, and the diagnostic testing UI may be presented within the web browser.

The test coordination server 130, in various embodiments, may include a test interface engine 132, a data standardization engine 134, a CDS engine 136, and a request engine 138.

The test interface engine 132 may configure various aspects of the diagnostic testing GUI 114. For example, the test interface engine 132 may configure a test selection UI for displaying a number of recommended diagnostic tests (also referred to as candidate diagnostic tests) for the user 120 to select from, an order entry UI for presenting and entering details related to a specific diagnostic test, and a results analysis UI for presenting data related to test results, including potential courses of actions (i.e., candidate treatments).

The data standardization engine 134 may standardize data from different sources so that it may be presented in a uniform way to the user 120. For example, the data standardization engine 134 may convert differing terms used by different test providers with the same meaning into a standard term for use in the order entry UI. The data standardization engine 134 may also convert data entered in the order entry UI (e.g., by the user 120 or retrieved from the EMR application 112) into a format expected by a test provider. The data standardization engine may also convert test results from different test providers into a standardized or uniform format for use by the test coordination server 130.

The CDS engine 136 may guide a physician in selecting diagnostic tests and courses of action appropriate for a patient. For example, based on patient information included in a request from the EMR application 112, the CDS engine 136 may propose a set of diagnostic tests (e.g., molecular tests for different biomarkers) from which the physician may choose. Based on the results of the tests and the patient information, the CDS engine 136 may also propose various courses of action specific to the patient and add contextual information to the test results (e.g., from a medical knowledgebase).

The request engine 138 may receive requests for diagnostic test information associated with a patient from the EMR application 112. The requests may include patient data for use by the request engine 138 and other components of the test coordination server 130. The request engine may also transmit diagnostic test requisitions based on the requests to the test provider server 150 and receive results for the diagnostic tests from the test provider server 150.

The test provider server 150, in various embodiments, may be a server executing software for receiving diagnostic test requisitions (also referred to as test orders) and transmitting diagnostic test results. For simplicity, one test provider server 150 is illustrated in FIGS. 1 and 2 and referenced throughout the present disclosure, but the test coordination server 130 may communicate with any number of test provider servers 150. For example, different test providers (e.g., laboratories) may each have their own test provider server 150. A single test provider server 150 may also provide services to multiple test providers (e.g., in a multitenant system, or where a third-party processes test requisitions and result delivery for multiple test providers).

FIG. 2 is a bock diagram illustrating a system 200 that includes a test coordination server 130, in accordance with various embodiments. The system also includes a physician device 110, and a test provider server 150.

As described with respect to FIG. 1, the physician device 110 may include an EMR application 112 and diagnostic testing GUI 114, which may be embedded within the EMR application 112, or hosted on the test coordination server 130 and presented on the physician device 110. The physician device may store and retrieve patient data from a medical records data store 210, which may internal or external to the physician device 110. The medical records data store may store patient information and administrative information relating to the use of the EMR application 112 (e.g., authentication information, user permissions, etc.). The patient information may include, for example, biographical information about the patient (e.g., name, birth date, etc.), medical history (e.g., medical conditions, allergies, surgeries, hospitalizations, etc.) including family medical history, medications taken by the patient, insurance information, diagnostic test results, and any number of other types of information related to a patient. In some embodiments, patient data (including, for example, test orders and test results) may also be stored in the test information data store 220 and/or CDS data store 222.

The EMR application 112 may transmit requests to the test coordination server 130 for diagnostic test information. Each request may include patient information relevant to the request. For example, EMR application 112 may transmit a request to load a test selection UI, a test order entry UI, or a results analysis UI, which may be received by the request engine 138 of the test coordination server 130. Each request may include a patient ID identifying the patient and medical information relevant to which tests or treatment options may be appropriate (e.g., symptoms and other medical history). Each request may include all available patient information from the EMR application 112 that may be used to populate various fields of the particular UI being launched, as described below. The EMR application 112 may also transmit complete or partially complete test requisitions to the test coordination server (e.g., when the diagnostic testing UI 114 is embedded within the EMR application 112).

The test coordination server 130 includes a test interface engine 132, a data standardization engine 134, a CDS engine 136, and a request engine 138. The test coordination server 130 may interact with a test information data store 220 and a CDS data store 222. The test information data store 220 and the CDS data store 222 may be internal or external to the test coordination server 130. For example, data store 220 and the CDS data store 222 may be databases, files, or other storage structures residing on a disk within the test coordination server, or on a different server or different servers.

The test information data store 220 may store diagnostic test definition data, which may include a plurality of test definitions for diagnostic tests supported by the test coordination server. Each test definition may define data specific to a diagnostic test, including the parameters required to complete a test requisition for the test, the test requisition format expected by a test provider, the content of an electronic questionnaire for obtaining required data from a user 120, and/or logic for presenting the questionnaire to the user. For example, the test information data store 220 may include a test definition for an epidermal growth factor receptor (EGFR) biomarker test, and the test coordination server 130 may include support for four test providers (e.g., laboratories) that perform the EGFR biomarker test, with each test provider expecting a requisition for the EGFR test in a different data format. Each test provider may refer to commonly required parameters by different terms or expect different values for a commonly required parameter (e.g., one provider may require a "TestID" of "EGFR-000-001" and a second provider may require a "test-identifier" of "ML-EGFR-XRZ01", where "TestID" and "test-identifier" are identifiers that uniquely identify the test within the respective test provider). Different test providers may also require different parameters to receive and process a test requisition (e.g., one lab may require a patient e-mail address as part of a test requisition, and a second lab may not). Accordingly, the test definition for the EGFR test may include various standardized parameters with mappings for different labs. For example, the EGFR test definition may include a ProviderTestID field with mappings to the test identifier parameters expected by the different labs. Each test definition may also include a section indicating which parameters are required, which parameters are optional, and which parameters are not supported by different test providers.

The CDS data store 222 may store data associated with a plurality of biomarker definitions and related medical conditions. For example, the CDS data store 222 may include entries for each biomarker for which test providers may test, along with a list of medical conditions associated with the biomarkers, information relating to the conditions, and treatment options appropriate when the existence of a particular biomarker is detected. For example, the CDS data store 222 may include an entry associating the EGFR biomarker with small-cell lung cancer, including potential courses of actions (e.g., treatment options and further testing appropriate when the biomarker is detected). The CDS data store 222 may be periodically updated (e.g., through the content updates from medical knowledgebase service providers).

The request engine 138 may receive requests for diagnostic test information associated with a patient from the EMR application 112. The requests may include patient data for use by the request engine 138 and other components of the test coordination server 130. For example, the request engine may receive a request to load a test selection UI for viewing and selecting from a list of candidate tests based on the patient data, a test order entry UI, for viewing and entering details for test requisition, or a results analysis UI, for viewing test results with associated medical information and proposed courses of action based on the test results and patient data. The patient data may include a patient ID identifying the patient all available patient information from the EMR application 112 that may be appropriate for the operations to be performed by the test coordination server 130 (e.g., a request to launch a UI may include information that may be used to automatically populate fields of the UI). For example, the patient data may include biographical data (e.g., name, birth date, phone number, address, etc.), insurance information, and medical information (e.g., a potential diagnosis for which tests are sought, allergies, comorbidities, etc.). Different types of requests may include different types of patient data. For example, patient data transmitted with a request to launch the test selection UI or order entry UI may include insurance information (e.g., for use in determining which test provider to use and for providing the insurance information to the test provider), but a request to launch the results analysis may omit insurance information from the patient data. The request engine may transmit diagnostic test requisitions based on the requests to the test provider server 150. Prior to transmitting a request, the request engine 138 may determine whether the user 120 causing the request to be transmitted (e.g., through the order entry UI) is authorized to submit requests (e.g., in combination with the EMR application 112, using administrative information stored within the medical records data store 210). The request engine 138 may also receive requests from the EMR application 112 to transmit complete or partially complete test requisitions (e.g., test requisition forms completed outside the order entry UI) to a test provider. The request engine 138 may receive results for diagnostic tests from the test provider server 150, process the results in combination with the data standardization engine 134 to generate results in a provider-agnostic standardized format, and transmit the processed results to the EMR application 112. The patient information, test results, and other medical information may be received and transmitted by the request engine 138 using, for example, the Fast Healthcare Interoperability Resources (FIHR) standard.

The CDS engine 136 may be used to provide guidance with respect to what diagnostic tests are appropriate for a patient, and what courses of action (i.e., treatments or follow-up tests) are appropriate based on the results of the diagnostic tests. The request engine 138 may transmit patient data included with a request (e.g., a request related to the order entry UI) to the CDS engine 136, and the CDS engine 136 may determine one or more diagnostic tests based on the request (i.e., the patient data included with the request) that may be appropriate for the patient's condition. The CDS engine 136 may search the CDS data store 222 to determine the appropriate tests. For example, if the patient data indicates the patient has been diagnosed with small-cell lung cancer, the CDS engine 136 may retrieve a record from the CDS data store 222 corresponding to small-cell lung cancer. The record may include a number of biomarkers that may be relevant in determining a treatment for small-cell lung cancer (e.g., EGFR and anaplastic lymphoma kinase (ALK) biomarkers). The CDS engine 136 may select each biomarker in the record and transmit an indication to the request engine indicating that diagnostic tests should be run for the presence of each selected biomarker. Each diagnostic test may be associated with a test definition stored in the test information data store 220, as described herein.

The CDS engine 136 may also determine one or more courses of action based on standardized results (i.e., test results received from a test provider and processed with the data standardization engine 134) and biomarker definitions. The CDS engine 136 may match a biomarker indicated in a standardized result to a number of courses of action using the CDS data store 222. For example, a standardized result may indicate the presence of the EGFR biomarker. The CDS engine 136 may retrieve a record corresponding to EGFR from the CDS data store 222, which may indicate a number of potential courses of actions (e.g., treatment options and/or follow-up tests) appropriate when EGFR is detected. The CDS engine 136 may retrieve additional medical information related to EGFR from the CDS data store 222, for example, side effects and predicted outcomes associated with a course of action. The CDS engine 136 may transmit the determined courses of action and/or additional medical information to the request engine.

The data standardization engine 134 may convert data associated with a diagnostic test into a test data requisition format associated with a test provider. The request engine 138 may invoke the data standardization engine 134 to convert the data associated with the diagnostic test. For example, the request engine 138 may invoke the data standardization engine 134 to convert data from the order entry UI (or received from the EMR application 112) in preparation for transmission to a test provider server 150. The data from the order entry UI may be stored in stored in a standardized (or uniform) format used by the test coordination server 130 (e.g., in the medical records data store 210 or the test information data store 220). The data standardization engine 134 may retrieve a test definition corresponding to the diagnostic test from the test information data store 220. The test definition may store mappings between parameters in the standardized data format used by the test coordination server 130 and the parameters in the data format expected by the test provider server 150. The data standardization engine 134 may use those mappings to convert the standardized data into a provider-specific format expected by the provider server 150. The request engine 138 may then transmit a test requisition for the test in the provider-specific format.

The data standardization engine 134 may also generate a standardized result based on a result received from the test provider server 150 (e.g., a result received by the request engine 138). The data standardization engine may convert data associated with the received result into the standardized format used by the test coordination server 130. For example, the data standardization engine 134 may retrieve the test definition corresponding to the result from the test information data store 220. The test definition may include a mapping for converting parameters from the provider-specific format in which the data is received from the test provider server 150 into the standardized format used by the test coordination server 130. The data standardization engine 134 may then send the standardized result to the request engine 138.

The test interface engine 132 may configure UIs of the test coordination server (e.g., the test selection UI, order entry UI, and results analysis UI), including selecting which fields to display and/or populating the fields with data (e.g., with patient data included in a request). For example, the test interface engine 132 may receive from the request engine 138 data related to candidate diagnostic tests (e.g., determined by the CDS engine 136) that may be appropriate for a patient, based on patient information included in a request to the request engine 138. The test interface engine 132 may populate a set of candidate diagnostic test GUI fields of the test selection UI with entries corresponding to each candidate diagnostic test. The test interface engine may also propose one or more test providers from which to request each test (e.g., based on insurance information included with the patient data). The test interface may sort the providers based on various criteria (e.g., cost to the patient, average time to complete the test, etc.). When the user 120 selects a candidate diagnostic test from one of the fields, the test interface engine may verify that the user is authorized to initialize a diagnostic test order for use in creating a test requisition. If the user is authorized, the test interface engine 132 may coordinate with the request engine 138 to present the order entry UI. The order entry UI may be configured based on the test selected and the test provider selected. In some embodiments, the test interface engine 132 may select a test provider (e.g., based on insurance affiliation and/or cost) if the user 120 does not.

The test interface engine 132 may populate a number of patient information fields and test requisition fields of the order entry UI as illustrated in FIGS. 3 and 4. For example, the test interface engine 132 may populate the patient information fields using patient data (e.g., patient name, birthdate, condition, etc.) received by the request engine 138 as part of a request. The test interface engine 132 may populate test requisition fields based on the patient data and test definition associated with the diagnostic test being requested, for example, a test name and/or ID and details specific to the test provider to which the test requisition can be transmitted. The test interface engine 132 may use consistent terminology when referring to data to be entered in the GUI fields independent of which test provider is selected, but the fields presented by vary based on the requirements of the test provider. The test interface engine 132 may leave a number of GUI fields blank for data entry by the user 120, when, for example, the information belonging in a GUI filed could not be determined based on the patient data or test definition.

The test interface engine 132 may also generate test requisitions based on requests received by the request engine 138. For example, as described above, the test interface engine 132 may populate a number of fields of the order entry UI. Using the data from the order entry UI (including both the data populated by the test interface engine 132 and entered by the user 120), the test interface engine 132 may generate a test requisition. The test interface engine 132 may communicate with the request engine 138 and the data standardization engine 134 to convert the data from the order entry UI into a test requisition in a provider-specific format for transmission to a provider server 150.

The test interface engine 132 may also populate test result fields based on a standardized result and a test definition. For example, upon receiving a test result from a test provider server 150, the request engine 138 may coordinate with the data standardization engine 134 to standardize the test result (i.e., convert data from the test result into a uniform format used by the test coordination server) using the test definition (retrieved from the test information data store 220) corresponding to the test. The request engine may transmit the standardized result to the test interface engine 132, which may populate fields in the results analysis UI corresponding to the data in the standardized result. The test interface engine 132 may also populate recommended course of action fields of the results analysis UI based on courses of action determined by the CDS engine 136 as described above. For example, the test interface engine 132 may populate fields corresponding to recommended therapies and/or follow-up tests that may be appropriate.

FIG. 3 is an illustration of an exemplary order entry UI 300 for ordering a diagnostic test, in accordance with various embodiments. The order entry UI 300 may be presented within the diagnostic testing GUI 114, which as described above, may be embedded within the EMR application 112 and/or hosted on the test coordination server 130. The order entry UI 300 may be presented in response to selecting a diagnostic test from the test selection UI.

Fields of the order entry UI 300 may be populated by the test interface engine 132 based on patient data transmitted as part of a request by the EMR application 112 and on a test definition. For example, the patient fields 320 may be populated by the test interface 132 using patient data included in a request from the EMR application 112. As illustrated, the patient data may be used to populate patient data fields including patient name, sex, date of birth, and medial record number (MRN, i.e., a patient ID) fields. Similarly, the test interface engine may populate a number of test requisition fields 310. For example, the test name, version, lab name, address, and phone number fields may be populated with data obtained from the test definition (retrieved from the test information data store 220) corresponding to the test named "OncoMP-10001." The content of other fields, for example, the order, status, last status change, and created fields may be automatically generated by the test interface engine based on when an event occurred. The order entry UI may also include information about the practice and medical professional requesting the test, which may be populated from data included in a request from the medical records data store 210. The practice fields 330 and ordering physician fields 340 may be populated with this data. Some fields may be included in a collapsed UI element 360, and become visible when the collapsed UI element 360 is expanded. For example, collapsed UI element 360 includes clinical information fields, as illustrated in FIG. 4.

Once the user 120 has verified the information in the order entry UI 300 and entered any additional required information that was not populated by the test interface engine 132, the user 120 may sign the test order, for example, using the sign button 350, which may cause the test interface engine to verify that all required information has been provided, finalize the order, and generate the test requisition. Prior to signing the test order and generating the test requisition, the test interface engine 132 may determine whether the user 120 is authorized to request transmission of the test order (e.g., using administrative information stored in the medical records data store 210).

FIG. 4 is an illustration of an exemplary order entry UI 400 for entering clinical data for a diagnostic test order, in accordance with various embodiments. The order entry UI 400 illustrates UI element 360 of FIG. 3 when expanded from the collapsed state illustrated in FIG. 3. As in FIG. 3, the test interface engine 132 may populate a number of patient information fields 420 and test requisition fields 430 based on patient data received in a request from the EMR application 112 and a test definition. The test interface engine 132 may present the patient information fields 420 and test requisition fields 430 in a uniform format, regardless of the test provider to which the test requisition may be transmitted. However, one test provider may require different parameters than a second provider, as the test interface engine 132 may determine from the test definition. For example, the test provider for which the order displayed in FIGS. 3 and 4 is being prepared may require details about a tumor size and grade, which a second test provider may not. Accordingly, the test interface engine may generate a "Lymph Node Tumor Details" section 435 for the test order being prepared, but may not include the section 435 if the test order was being prepared for the second test provider. The test interface engine 132 may also include guidance 440 for the user 120 completing the test order (e.g., for elements of the order entry UI 400 which are not populated by the test interface engine 132). As illustrated in FIG. 4, the guidance 440 may be specific to the test provider for which the test order is being prepared. The guidance 440 may be based on the test definition corresponding to the test, and may further be based on information stored in the CDS data store. For example, in addition to providing test-provider-specific support, the test interface engine 132 may retrieve information from a knowledge base maintained in the CDS data store 222 (e.g., definitions for terminology).

FIG. 5 is an illustration of exemplary results analysis UIs 510a, 510b, and 510c for providing analysis of diagnostic test results and recommending courses of treatment, in accordance with various embodiments. The results analysis UIs 510a, 510b, and 510c may be presented within the diagnostic test GUI 114, which as described above, may be embedded within the EMR application 112 and/or hosted on the test coordination server 130. Results analysis UIs 510a, 510b, and 510c each depict test results and analysis for an exemplary patient for tests taken at different points in time during the progression of the patient's disease. Results analysis UI 510a corresponds to an initial diagnostic test, results analysis UI 510b corresponds to a diagnostic test performed a year after the initial diagnostic test, and results analysis UI 510c corresponds to a diagnostic test performed two years after the initial diagnostic test. The result analysis UIs 510a, 510b, and 510c each include a therapies section (520a, 520b, and 520c), a findings section (530a, 530b, and 530c), and a biomarkers section (540a, 540b, and 540c).

As discussed above with respect to FIG. 2, a request engine 138 may receive test results from a test provider server 150. In coordination with the data standardization engine 134, the request engine 138 may convert the results into a standard format for use by the test coordination server 130. The CDS engine 136 may then determine one or more courses of action based on the standardized results and on biomarker definitions retrieved from the CDS data store 222. For example, results analysis UI 510a illustrates in biomarkers section 540a that the results indicate the presence of an EGFR biomarker. The CDS engine 136 may search the CDS data store 222 for a record corresponding to the EGFR biomarker. Upon finding a matching record, the CDS engine 136 may determine from the matching record that the EGFR biomarker corresponds to the finding statement illustrated in findings section 530a. The CDS engine 136 may also determine based on the record that the therapies in therapies section 520a are recommended courses of action for treating a tumor that includes the EGFR biomarker. The CDS engine 136 may transmit its determinations (e.g., through the request engine 138) to the test interface engine 138 which may populate the therapies section 520a, findings section 530a, and biomarkers 540a accordingly.

As the patient's disease progresses and more tests are performed, the CDS engine 136 may revise its recommended courses of action (e.g., therapies) and findings. For example, results analysis UI 510b illustrates an additional EGFR biomarker in the biomarkers section 540b, corresponding to an additional finding statement in the findings section 530b. Using the same procedure described with respect to results analysis UI 510a, the CDS engine 136 may determine that a different, single course of action is appropriate, as illustrated in the therapies section 520b. Similarly, as illustrated in results analysis UI 510c, based on tests performed two years after the initial diagnostic test, a third biomarker has been detected and included in biomarkers section 540c, resulting in the CDS engine 136 generating a finding statement as illustrated in findings section 530c, indicating the patient is a poor candidate for TKI-based therapies. Accordingly, the CDS engine 136 determined no recommended therapies are appropriate, and the test interface engine 132 populated the therapies section 520c with an indication that no therapies were found.

Figure 6:
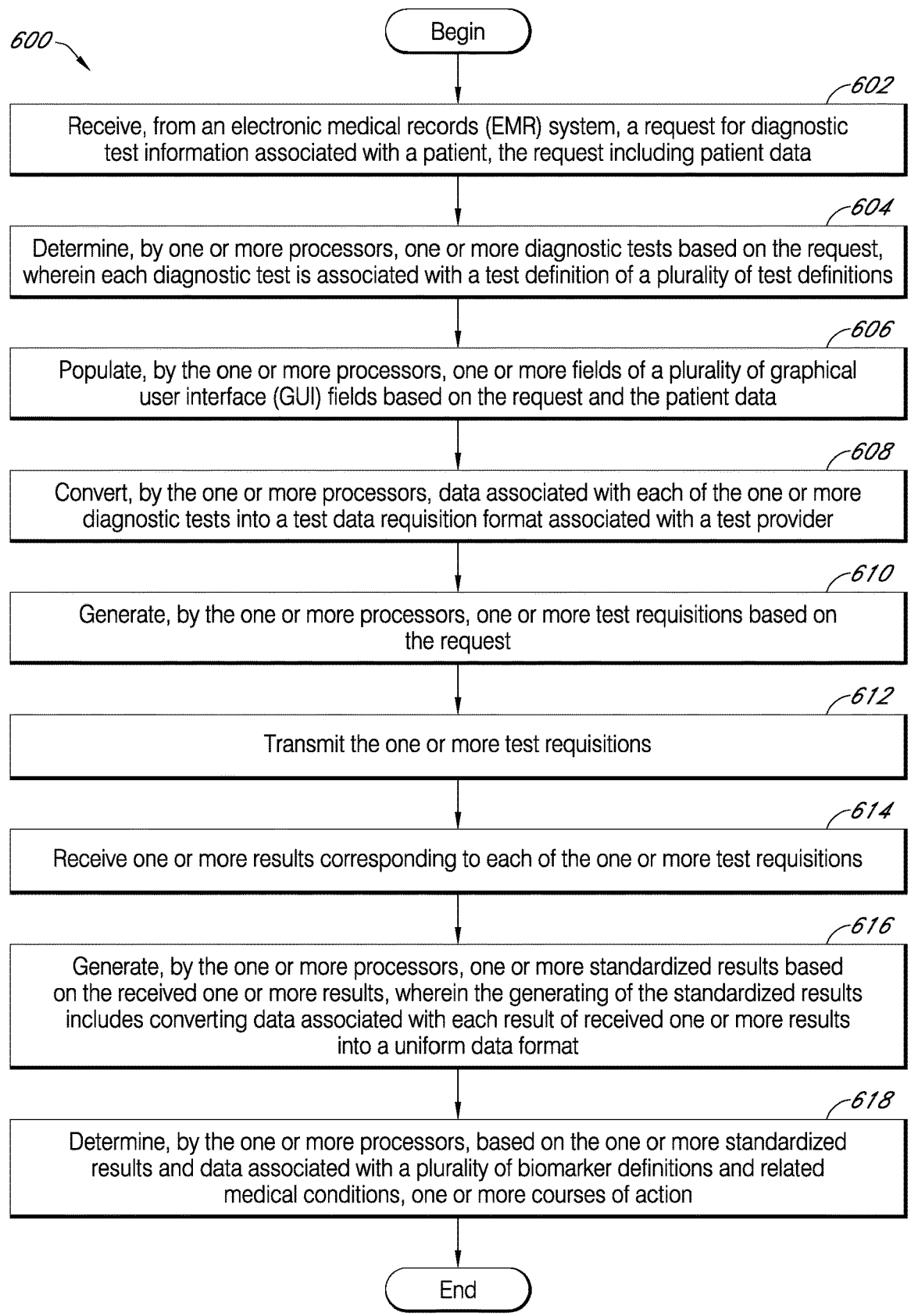
FIG. 6 is an exemplary flowchart showing a method for providing CDS, in accordance with various embodiments.

FIG. 6 is an exemplary flowchart showing a method 600 for providing CDS, in accordance with various embodiments.

At step 602, the method 600 receives (e.g., via the request engine 138) a request from an EMR system (e.g., the EMR application 112) for diagnostic test information, the request including patient data. The patient data may include one or more of demographic information (e.g., name, birth date, etc.), symptoms, medical history (e.g., diagnoses, other medical conditions, allergies, surgeries, hospitalizations, etc.), behavioral characteristics, diagnostic test orders, or diagnostic test results. For example, the request engine 138 may receive a request to load a test selection UI, a test order entry UI, or a results analysis UI. Each request may include a patient ID or patient number identifying the patient and medical information relevant which tests or treatment options may be appropriate. Each request may include all available patient information from the EMR application 112 that may be used to populate various fields of the particular UI being launched, as described below. The request engine 138 may also receive complete or partially complete test requisitions for processing and transmission to a provider (e.g., to a test provider server 150). In some embodiments, the request engine 138 may request some or all of the patient data from the EMR application 112. For example, the initial request from the EMR application 112 may not include all of the patient data that may be used to process the initial request. After receiving the request from the EMR application 112, the request engine 138 may send a request to the EMR application 112 for relevant patient data (e.g., based on the patient ID or patient number). In response, the request engine 138 may receive some or all of the patient data from the EMR application 112, separate from the initial request.

At step 604, the method 600 determines (e.g., using a CDS engine 136) one or more diagnostic tests based on the request. Each diagnostic test is associated with a test definition of a plurality of test definitions. Each test definition may define data specific to a diagnostic test, including the parameters required to complete a test requisition for the test, the test requisition format expected by the test provider, the content of an electronic questionnaire for obtaining required data from a user 120, and/or logic for presenting the questionnaire for the user. For example, a diagnostic test may be associated with test definition for an EGFR biomarker test. Various test providers may be capable of performing the EGFR biomarker test, with each test provider expecting a requisition for the EGFR test in a different data format. Each test provider may refer to commonly required parameters by different terms or expect different values for a commonly required parameter. Different test providers may also require different parameters to receive and process a test requisition (e.g., one lab may require a patient phone number as part of a requisition, and a second lab may not). Accordingly, the test definition for the EGFR test may include various standardized parameters with mappings for different labs. Each test definition may also include a section indicating which parameters are required, which parameters are optional, and which parameters are not supported by different test providers.

In various embodiments, determining the one or more diagnostic tests may include determining, based on the patient data, one or more biomarkers, wherein the one or more diagnostic tests are designed to detect the one or more biomarkers. For example, the CDS engine 136 may maintain records (e.g., in a CDS data store 222) associating a medical condition with biomarkers that may be relevant in the treatment of the medical condition. Continuing the example of the EGFR biomarker test, a patient may be diagnosed with small-cell lung cancer. The patient data received by the request engine 138 along with a request to launch the test selection UI may include the small-cell lung cancer diagnosis. The CDS engine 136 may retrieve a record from the CDS data store 222 for small-cell lung cancer, which may include a list of relevant biomarkers, including EGFR. The one or more diagnostic tests may correspond to each biomarker in the record for small-cell lung cancer. The CDS engine 136 may omit some biomarker tests from the determined tests, for example, when it determines the biomarker test would not be helpful (e.g., if the patient was already tested for the biomarker recently).

At step 606, the method 600 may populate (e.g., using the test interface engine 132) one or more fields of a plurality of graphical user interface (GUI) fields based on the request and the patient data. The plurality of GUI fields may be presented in the GUI of the EMR system. The method 600 may populate, based on the request and each test definition associated with the one or more diagnostic tests, a set of one or more patient information fields of the plurality of GUI fields. For example, the test interface engine may populate GUI fields with the patient's name, birthdate, weight, diagnosis, etc. throughout the test selection UI, order entry UI, results analysis UI, and other UIs related to the test coordination server 130.

In some embodiments, the method 600 may populate (e.g., using the test interface engine 132), based on the request, a set of one or more candidate diagnostic test fields of the plurality of GUI fields. For example, the test interface engine may populate a GUI list element that includes a number of fields with the names of each of the one or more diagnostic tests determined by the CDS engine 136. Activating a field (e.g., clicking or tapping on a field) may launch the order entry UI, configured for the diagnostic test corresponding to the field.

In some embodiments, the method 600 may populate (e.g., using the test interface engine 132), based on each test definition associated with the one or more diagnostic tests, a set of one or more test requisition fields of the plurality of GUI fields. For example, based on a test definition associated with the diagnostic test selected from the test selection UI, the test interface engine 132 may configure the order entry UI with test requisition fields for entering the data indicated by the test definition, and populate the fields. For example, the test interface engine 132 may populate a test ID field based on the test definition, a field indicating the reason for the test based on patient data included in the request. In some embodiments, the test interface engine 132 may determine whether a user 120 is authorized to initialize a diagnostic test order, wherein a test requisition of the one or more test requisitions is based on the diagnostic test order, and present the order entry UI only if the user 120 is authorized.

In some embodiments, the method 600 may populate (e.g., using the test interface engine 132), based on one or more standardized results and each test definition associated with the one or more diagnostic tests, a set of one or more test result fields of the plurality of GUI fields. The method 600 may also populate, based at least on the one or more courses of action, a set of one or more recommended course of action fields of the plurality of GUI fields. The test result fields and recommended course of action fields may be part of the results analysis UI. For example, as described in detail with respect to FIG. 2 and below, the request engine 138 may coordinate with the data standardization engine 134 to standardize results received from the test provider server 150 into a uniform format. The test interface engine 132 may populate test result fields (e.g., fields corresponding to the name of a biomarker and whether the biomarker was detected) using data from the standardized results. The test interface engine 132 may also populate recommended course of action fields with potential treatments determined by the CDS engine 136 based on the standardized test results.

At step 608, the method 600 converts data associated with each of the one or more diagnostic tests into a test data requisition format associated with a test provider. For example, the request engine 138 may invoke the data standardization engine 134 to convert data from the order entry UI in preparation for transmission to the test provider server 150. The data from the order entry UI may be stored in stored in a standardized (or uniform) format used by the test coordination server 130. The data standardization engine 134 may retrieve a test definition corresponding to the diagnostic test from the test information data store 220. The test definition may store mappings between parameters in the standardized data format used by the test coordination server 130 and the parameters in the data format expected by the test provider server 150. The data standardization engine 134 may use those mappings to convert the standardized data into a provider-specific format expected by the test provider server 150.

At step 610, the method 600 generates (e.g., using the request engine 138) one or more test requisitions based on the request. The request engine 138 may validate each test requisition, for example, by confirming that all of the information required by the test provider to which the requisition may be sent has been completed.

At step 612, the method 600 transmits the one or more test requisitions (e.g., using the request engine 138). The test requisitions may be transmitted to a diagnostic test provider (e.g., the test provider server 150 of the test provider). In some embodiments, the request engine 138 may determine whether a user is authorized to request transmission of the one or more test requisitions, and transmit the one or more test requisitions only if the user is authorized.

At step 614, the method 600 receives (e.g., by the request engine) one or more results corresponding to each of the one or more test requisitions. The test requisitions may be received from a diagnostic test provider (e.g., the test provider server 150 of the test provider).

At step 616, the method 600 generates one or more standardized results (e.g., using the data standardization engine 134) based on the received one or more results, wherein the generating of the standardized results includes converting data associated with each result of received one or more results into a uniform data format. For example, the data standardization engine 134 may retrieve the test definition corresponding to the result from the test information data store 220. The test definition may include a mapping for converting parameters from the provider-specific format in which the data is received from the test provider server 150 into the standardized format used by the test coordination server 130.

At step 618, the method 600 determines (e.g., using the CDS engine 136), based on the one or more standardized results and data associated with a plurality of biomarker definitions and related medical conditions, one or more courses of action. The CDS engine 136 may match a biomarker indicated in a standardized result to a number of courses of action using the CDS data store 222. For example, a standardized result may indicate the presence of the EGFR biomarker. The CDS engine 136 may retrieve a record corresponding to the EGFR biomarker from the CDS data store 222, which may indicate a number of potential courses of actions (e.g., treatment options and/or follow-up tests) appropriate when EGFR is detected. The determined courses of action may include each potential course of action in the record, or a different number of courses of action. For example, based on patient data, the CDS engine 136 may determine a particular course of action in the record is not appropriate for the patient (e.g., if the patient is allergic to an indicated treatment, if an indicated treatment would be overly dangerous to the patient because of a comorbidity, or if an indicated treatment would be ineffective for the patient). The method 600 may then transmit (e.g., using the request engine 138), to the EMR system, the standardized results.

In various embodiments, the methods for providing CDS with respect to choosing and ordering diagnostic tests, receiving and interpreting diagnostic test results, and determining appropriate courses of treatment for a patient's condition can be implemented via computer software or hardware. That is, as depicted in FIG. 2, the methods disclosed herein can be implemented on a computing device (i.e., test coordination server 130) that includes a test interface engine 132, a data standardization engine 134, a CDS engine 136, and a request engine 138. In various embodiments, the test coordination server 130 can be communicatively connected to a test information data store 220, a CDS data store 222, a physician device 110, and a test provider server 150, via a direct connection or through a network connection.

It should be appreciated that the various engines depicted in FIG. 2 can be combined or collapsed into a single engine, component or module, depending on the requirements of the particular application or system architecture. Moreover, in various embodiments, the test interface engine 132, data standardization engine 134, CDS engine 136, and request engine 138 can comprise additional engines or components as needed by the particular application or system architecture.

Figure 7:
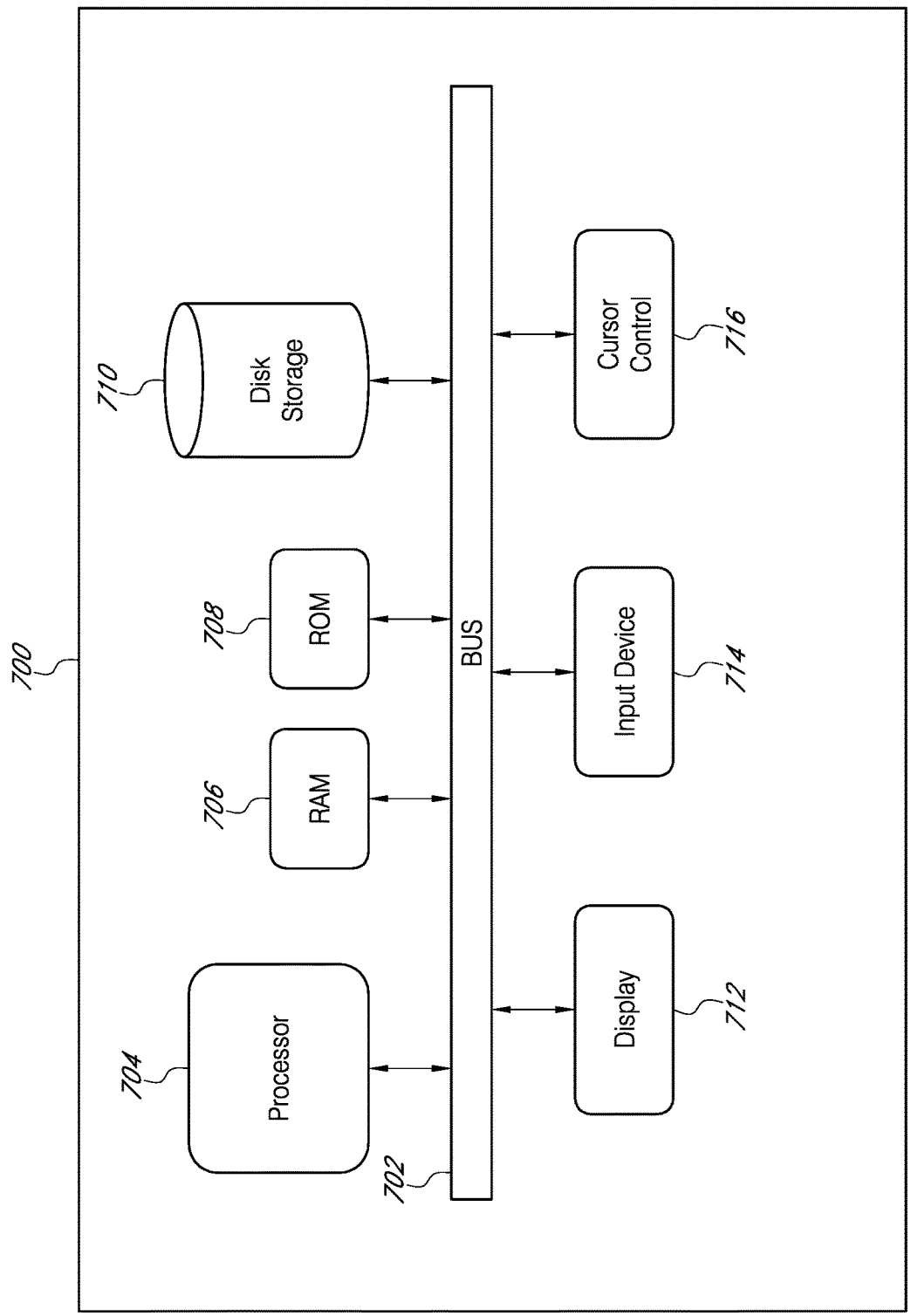
FIG. 7 is a block diagram that illustrates a computer system, in accordance with various embodiments.

FIG. 7 is a block diagram that illustrates a computer system, in accordance with various embodiments. In various embodiments of the present teachings, computer system 700 can include a bus 702 or other communication mechanism for communicating information, and a processor 704 coupled with bus 702 for processing information. In various embodiments, computer system 700 can also include a memory, which can be a random-access memory (RAM) 706 or other dynamic storage device, coupled to bus 702 for determining instructions to be executed by processor 704. Memory also can be used for storing temporary variables or other intermediate information during execution of instructions to be executed by processor 704. In various embodiments, computer system 700 can further include a read only memory (ROM) 708 or other static storage device coupled to bus 702 for storing static information and instructions for processor 704. A storage device 710, such as a magnetic disk or optical disk, can be provided and coupled to bus 702 for storing information and instructions.

In various embodiments, computer system 700 can be coupled via bus 702 to a display 712, such as a cathode ray tube (CRT) or liquid crystal display (LCD), for displaying information to a computer user. An input device 714, including alphanumeric and other keys, can be coupled to bus 702 for communicating information and command selections to processor 704. Another type of user input device is a cursor control 716, such as a mouse, a trackball or cursor direction keys for communicating direction information and command selections to processor 704 and for controlling cursor movement on display 712. This input device 714 typically has two degrees of freedom in two axes, a first axis (i.e., x) and a second axis (i.e., y), that allows the device to specify positions in a plane. However, it should be understood that input devices 714 allowing for 3-dimensional (x, y and z) cursor movement are also contemplated herein.

Consistent with certain implementations of the present teachings, results can be provided by computer system 700 in response to processor 704 executing one or more sequences of one or more instructions contained in memory 706. Such instructions can be read into memory 706 from another computer-readable medium or computer-readable storage medium, such as storage device 710. Execution of the sequences of instructions contained in memory 706 can cause processor 704 to perform the processes described herein. Alternatively, hard-wired circuitry can be used in place of or in combination with software instructions to implement the present teachings. Thus, implementations of the present teachings are not limited to any specific combination of hardware circuitry and software.

The term "computer-readable medium" (e.g., data store, data storage, etc.) or "computer-readable storage medium" as used herein refers to any media that participates in providing instructions to processor 704 for execution. Such a medium can take many forms, including but not limited to, non-volatile media, volatile media, and transmission media. Examples of non-volatile media can include, but are not limited to, optical, solid state, magnetic disks, such as storage device 710. Examples of volatile media can include, but are not limited to, dynamic memory, such as memory 706. Examples of transmission media can include, but are not limited to, coaxial cables, copper wire, and fiber optics, including the wires that comprise bus 702.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, or any other tangible medium from which a computer can read.

In addition to computer readable medium, instructions or data can be provided as signals on transmission media included in a communications apparatus or system to provide sequences of one or more instructions to processor 704 of computer system 700 for execution. For example, a communication apparatus may include a transceiver having signals indicative of instructions and data. The instructions and data are configured to cause one or more processors to implement the functions outlined in the disclosure herein. Representative examples of data communications transmission connections can include, but are not limited to, telephone modem connections, wide area networks (WAN), local area networks (LAN), infrared data connections, NFC connections, etc.

It should be appreciated that the methodologies described herein flow charts, diagrams and accompanying disclosure can be implemented using computer system 700 as a stand-alone device or on a distributed network of shared computer processing resources such as a cloud computing network.

The methodologies described herein may be implemented by various means depending upon the application. For example, these methodologies may be implemented in hardware, firmware, software, or any combination thereof. For a hardware implementation, the processing unit may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, electronic devices, other electronic units designed to perform the functions described herein, or a combination thereof.

In various embodiments, the methods of the present teachings may be implemented as firmware and/or a software program and applications written in conventional programming languages such as C, C++, Python, etc. If implemented as firmware and/or software, the embodiments described herein can be implemented on a non-transitory computer-readable medium in which a program is stored for causing a computer to perform the methods described above. It should be understood that the various engines described herein can be provided on a computer system, such as computer system 700, whereby processor 704 would execute the analyses and determinations provided by these engines, subject to instructions provided by any one of, or a combination of, memory components 706/708/710 and user input provided via input device 714.

RECITATIONS OF SOME EMBODIMENTS OF THE PRESENT DISCLOSURE

Embodiment 1: A method of providing clinical decision support, comprising: receiving, by one or more processors from an electronic medical records (EMR) system, a request for diagnostic test information associated with a patient, the request including patient data; determining, by the one or more processors, one or more diagnostic tests based on the request, wherein each diagnostic test is associated with a test definition of a plurality of test definitions; populating, by the one or more processors, one or more fields of a plurality of graphical user interface (GUI) fields based on the request and the patient data; converting, by the one or more processors, data associated with each of the one or more diagnostic tests into a test data requisition format associated with a test provider; generating, by the one or more processors, one or more test requisitions based on the request; transmitting, by the one or more processors, the one or more test requisitions; receiving, by the one or more processors, one or more results corresponding to each of the one or more test requisitions, generating, by the one or more processors, one or more standardized results based on the received one or more results, wherein the generating of the standardized results includes converting data associated with each result of received one or more results into a uniform data format; and determining, by the one or more processors, based on the one or more standardized results and data associated with a plurality of biomarker definitions and related medical conditions, one or more courses of action.

Embodiment 2: The method of embodiment 1, wherein the transmitting of the one or more test requisitions includes transmitting the one or more test requisitions to a diagnostic test provider and the receiving of the one or more results includes receiving the one or more results from the diagnostic test provider.

Embodiment 3: The method of embodiment 1 or 2, further comprising: determining whether a user is authorized to initialize a diagnostic test order, wherein a test requisition of the one or more test requisitions is based on the diagnostic test order.

Embodiment 4: The method of any of embodiments 1-3, further comprising: determining whether a user is authorized to request transmission of the one or more test requisitions, wherein the transmitting of the one or more test requisitions is based on the determining whether the user is authorized.

Embodiment 5: The method of any of embodiments 1-4, transmitting, to the EMR system, the standardized results.

Embodiment 6: The method of any of embodiments 1-5, further comprising: populating, based on the request and each test definition associated with the one or more diagnostic tests, a set of one or more patient information fields of the plurality of GUI fields.

Embodiment 7: The method of any of embodiments 1-6, further comprising: populating, based on the request, a set of one or more candidate diagnostic test fields of the plurality of GUI fields.

Embodiment 8: The method of any of embodiments 1-7, further comprising: populating, based on each test definition associated with the one or more diagnostic tests, a set of one or more test requisition fields of the plurality of GUI fields.

Embodiment 9: The method of any of embodiments 1-8, further comprising, populating, based on the one or more standardized results and each test definition associated with the one or more diagnostic tests, a set of one or more test result fields of the plurality of GUI fields.

Embodiment 10: The method of any of embodiments 1-9, further comprising: populating, based at least on the one or more courses of action, and a set of one or more recommended course of action fields of the plurality of GUI fields.

Embodiment 11: The method of any of embodiments 1-10, wherein the plurality of GUI fields is presented in a GUI of the EMR system.

Embodiment 12: The method of any of embodiments 1-11, wherein the determining of the one or more diagnostic tests comprises: determining, based on the patient data, one or more biomarkers, wherein the one or more diagnostic tests are designed to detect the one or more biomarkers.

Embodiment 13: The method of any of embodiments 1-12, wherein the patient data includes one or more of demographic information, insurance coverage information, symptoms, medical history, behavioral characteristics, diagnostic test orders, or diagnostic test results.

Embodiment 14: A system, comprising: a test information data store for storing diagnostic test definition data including a plurality of test definitions; a clinical decision support data store for storing data associated with a plurality of biomarker definitions and related medical conditions; and a computing device communicatively connected to the test information data store and the clinical decision support data store comprising a request engine, a clinical decision support engine, a data standardization engine, and a test interface engine, the system configured to perform the methods of aspects 1-13.

Embodiment 15: A non-transitory machine-readable medium having stored thereon machine-readable instructions executable to cause a machine to perform the methods of embodiments 1-13.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

In describing the various embodiments, the specification may have presented a method and/or process as a particular sequence of steps. However, to the extent that the method or process does not rely on the particular order of steps set forth herein, the method or process should not be limited to the particular sequence of steps described, and one skilled in the art can readily appreciate that the sequences may be varied and still remain within the spirit and scope of the various embodiments.

What is claimed is:

1. A method of providing clinical decision support, comprising:
receiving, by one or more processors of a test coordination server, a request from a physician device for diagnostic test information associated with a patient from an electronic medical records (EMR) system, the request including patient data;
determining, by the one or more processors of the test coordination server, one or more diagnostic tests based on the request, wherein each diagnostic test includes at least one test definition;
generating, by the one or more processors of the test coordination server, one or more fields of a plurality of graphical user interface (GUI) fields of a GUI of the EMR system, the GUI comprising a hyperlink for accessing capabilities of a test coordination server;
receiving, by the one or more processors of the test coordination server, an activation of the hyperlink;
in response to receiving the activation of the hyperlink, generating, by the one or more processors of the test coordination server, a diagnostic testing GUI within the GUI of the EMR system, wherein the diagnostic testing GUI is hosted by the test coordination server;
receiving, by the one or more processors of the test coordination server, a selection of the one or more diagnostic tests via the diagnostic testing GUI;
converting, by the one or more processors of the test coordination server, data associated with each of the one or more diagnostic test selection into a test data requisition format associated with a test provider, the converting including:
determining whether the test data requisition format associated with the test provider includes a different parameter than those found in a uniform data format;
generating a field in the diagnostic testing GUI within the GUI of the EMR system to receive information on the different parameter when the test data requisition format is determined to include a different parameter than those found in the uniform data format; and
receiving the information on the different parameter at the field in the diagnostic testing GUI;
generating, by the one or more processors of the test coordination server, one or more test requisitions based on the request; and
transmitting, by the one or more processors of the test coordination server, the one or more test requisitions to a test provider server.

2. The method of claim 1, further comprising:
receiving, by the one or more processors of the test coordination server, one or more results corresponding to each of the one or more test requisitions;
generating, by the one or more processors of the test coordination server, one or more standardized results based on the received one or more results, wherein the generating of the one or more standardized results includes converting data associated with each result of received one or more results into a uniform data format; and
determining, by the one or more processors of the test coordination server, based on the one or more standardized results and data associated with a plurality of biomarker definitions and related medical conditions, one or more courses of action.

3. The method of claim 1, further comprising:
determining to initialize a diagnostic test order, wherein a test requisition of the one or more test requisitions is based on the diagnostic test order.

4. The method of claim 1, further comprising:
determining to request transmission of the one or more test requisitions, wherein the transmitting of the one or more test requisitions is based on the determining whether a user of the physician device is authorized.

5. The method of claim 1, further comprising:
transmitting, to the EMR system, the standardized results.

6. The method of claim 1, further comprising:
generating, based on the request and each test definition associated with the one or more diagnostic tests, a set of one or more patient information fields of the plurality of GUI fields.

7. The method of claim 1, further comprising:
generating, based on the request, a set of one or more candidate diagnostic test fields of the plurality of GUI fields.

8. The method of claim 1, further comprising:
generating, based on each test definition associated with the one or more diagnostic tests, a set of one or more test requisition fields of the plurality of GUI fields.

9. The method of claim 1, further comprising:
generating, based on the one or more standardized results and each test definition associated with the one or more diagnostic tests, a set of one or more test result fields of the plurality of GUI fields.

10. The method of claim 1, further comprising:
generating, based at least on the one or more courses of action, and a set of one or more recommended course of action fields of the plurality of GUI fields.

11. The method of claim 1, wherein the plurality of GUI fields is presented in a GUI of the EMR system.

12. The method of claim 1, wherein the determining of the one or more diagnostic tests comprises:
determining, based on the patient data, one or more biomarkers, wherein the one or more diagnostic tests are designed to detect the one or more biomarkers.

13. The method of claim 1, wherein the patient data includes one or more of demographic information, insurance coverage information, symptoms, medical history, behavioral characteristics, diagnostic test orders, or diagnostic test results.

14. A system for providing clinical decision support, comprising:

a test coordination server configured to perform operations, comprising:
  receiving a request from a physician device for diagnostic test information associated with a patient from an electronic medical records (EMR) system, the request including patient data;
  determining one or more diagnostic tests based on the request, wherein each diagnostic test includes at least one test definition;
  generating one or more fields of a plurality of graphical user interface (GUI) fields of a GUI of the EMR system, the GUI comprising a hyperlink for accessing capabilities of a test coordination server;
  receiving an activation of the hyperlink;
  in response to receiving the activation of the hyperlink, generating a diagnostic testing GUI within the GUI of the EMR system, wherein the diagnostic testing GUI is hosted by the test coordination server;
  receiving a selection of the one or more diagnostic tests via the diagnostic testing GUI;
  converting data associated with each of the one or more diagnostic test selection into a test data requisition format associated with a test provider, the converting including:
    determining whether the test data requisition format associated with the test provider includes a different parameter than those found in a uniform data format;
    generating a field in the diagnostic testing GUI within the GUI of the EMR system to receive information on the different parameter when the test data requisition format is determined to include a different parameter than those found in the uniform data format; and
    receiving the information on the different parameter at the field in the diagnostic testing GUI;
  generating one or more test requisitions based on the request; and
  transmitting the one or more test requisitions to a test provider server.

15. The system of claim 14, wherein the transmitting of the one or more test requisitions includes transmitting the one or more test requisitions to a diagnostic test provider and the receiving of the one or more results includes receiving the one or more results from the diagnostic test provider.

16. The system of claim 14, wherein the test interface engine is further configured to determine whether a user of the physician device is authorized to initialize a diagnostic test order, wherein a test requisition of the one or more test requisitions is based on the diagnostic test order.

17. The system of claim 14, wherein the determining of the one or more diagnostic tests comprises:
  determining, based on the patient data, one or more biomarkers, wherein the one or more diagnostic tests are designed to detect the one or more biomarkers.

18. A non-transitory machine-readable medium having stored thereon machine-readable instructions executable to cause a machine to perform operations for providing clinical decision support, the operations comprising:
  receiving, by one or more processors of a test coordination server, a request from a physician device for diagnostic test information associated with a patient from an electronic medical records (EMR) system, the request including patient data;
  determining, by the one or more processors of the test coordination server, one or more diagnostic tests based on the request, wherein each diagnostic test includes at least one test definition;
  generating, by the one or more processors of the test coordination server, one or more fields of a plurality of graphical user interface (GUI) fields of a GUI of the EMR system, the GUI comprising a hyperlink for accessing capabilities of a test coordination server;
  receiving, by the one or more processors of the test coordination server, an activation of the hyperlink;
  in response to receiving the activation of the hyperlink, generating, by the one or more processors of the test coordination server, a diagnostic testing GUI within the GUI of the EMR system, wherein the diagnostic testing GUI is hosted by the test coordination server;
  receiving, by the one or more processors of the test coordination server, a selection of the one or more diagnostic tests via the diagnostic testing GUI;
  converting, by the one or more processors of the test coordination server, data associated with each of the one or more diagnostic test selection into a test data requisition format associated with a test provider;
  generating, by the one or more processors of the test coordination server, one or more test requisitions based on the request; and
  transmitting, by the one or more processors of the test coordination server, the one or more test requisitions to a test provider server.

19. The non-transitory machine-readable medium of claim 18, wherein the operations further comprise:
  determining whether a user of the physician device is authorized to initialize a diagnostic test order, wherein a test requisition of the one or more test requisitions is based on the diagnostic test order.

20. The non-transitory machine-readable medium of claim 18, wherein the patient data includes one or more of demographic information, insurance coverage information, symptoms, medical history, behavioral characteristics, diagnostic test orders, or diagnostic test results.

21. The system of claim 14, wherein the test coordination server is further configured to perform operations comprising:
  receiving one or more results corresponding to each of the one or more test requisitions,
  generating one or more standardized results based on the received one or more results, wherein the generating of the standardized results includes converting data associated with each result of received one or more results into a uniform data format; and
  determining based on the one or more standardized results and data associated with a plurality of biomarker definitions and related medical conditions, one or more courses of action.

22. The non-transitory machine-readable medium of claim 18, wherein the operations further comprise:
  receiving one or more results corresponding to each of the one or more test requisitions,
  generating one or more standardized results based on the received one or more results, wherein the generating of the standardized results includes converting data associated with each result of received one or more results into a uniform data format; and
  determining based on the one or more standardized results and data associated with a plurality of biomarker definitions and related medical conditions, one or more courses of action.

* * * * *